(12) United States Patent
Yamamoto et al.

(10) Patent No.: US 10,092,374 B2
(45) Date of Patent: Oct. 9, 2018

(54) DENTAL VIBRATION APPLICATION METHOD AND DENTAL VIBRATION APPLICATION DEVICE

(71) Applicants: JM Ortho Corporation, Tokyo (JP); TOHOKU UNIVERSITY, Miyagi (JP)

(72) Inventors: Teruko Yamamoto, Miyagi (JP); Takumi Sakimura, Osaka (JP); Shogo Fukushima, Osaka (JP)

(73) Assignees: JM Ortho Corporation, Tokyo (JP); TOHOKU UNIVERSITY, Miyagi (JP)

( * ) Notice: Subject to any disclaimer, the term of this patent is extended or adjusted under 35 U.S.C. 154(b) by 0 days.

(21) Appl. No.: 14/437,357

(22) PCT Filed: Oct. 18, 2013

(86) PCT No.: PCT/JP2013/006194
§ 371 (c)(1),
(2) Date: Apr. 21, 2015

(87) PCT Pub. No.: WO2014/064912
PCT Pub. Date: May 1, 2014

(65) Prior Publication Data
US 2015/0265375 A1    Sep. 24, 2015

(30) Foreign Application Priority Data
Oct. 22, 2012  (JP) ................................. 2012-233094

(51) Int. Cl.
*A61C 7/00*  (2006.01)
*A61C 7/08*  (2006.01)

(52) U.S. Cl.
CPC ................ *A61C 7/008* (2013.01); *A61C 7/08* (2013.01)

(58) Field of Classification Search
CPC .............. A61C 7/008; A61C 7/12; A61C 7/08
(Continued)

(56) References Cited

U.S. PATENT DOCUMENTS 4,123,844 A    11/1978 Kurz
4,229,165 A    10/1980 Kurz
(Continued)

FOREIGN PATENT DOCUMENTS

JP    2008-532563    8/2008
WO    2007/116654    10/2007
(Continued)

OTHER PUBLICATIONS

Noyes et al., "Measurement of Mechanical Mobility of Human Incisors With Sinusoidal Forces", J. Biomechanics, vol. 6, 1973, pp. 439-442.
(Continued)

*Primary Examiner* — Nicholas Lucchesi
(74) *Attorney, Agent, or Firm* — Studebaker & Brackett PC

(57) ABSTRACT

The present application discloses a vibration application method including a stage for contacting a contact portion with at least one tooth, and a stage for causing the contact portion to vibrate so as to impart displacement of 0.04 μm or more to the contact portion. The difference between the maximum value and minimum value of a vibrational load during the time the contact portion is vibrating may be 3 gf to 10 gf. The stage for contacting the contact portion with the at least one tooth may include a stage for contacting the contact portion with an orthodontic appliance attached to the at least one tooth.

4 Claims, 18 Drawing Sheets

(58) Field of Classification Search
USPC .................................................. 433/18, 24
See application file for complete search history.

(56) References Cited

U.S. PATENT DOCUMENTS

| | | | |
|---|---|---|---|
| 4,244,688 A | 1/1981 | Kurz | |
| 4,382,780 A * | 5/1983 | Kurz | A61C 7/06 433/5 |
| 5,967,784 A * | 10/1999 | Powers | A61C 7/00 433/2 |
| 6,832,912 B2 | 12/2004 | Mao | |
| 7,118,540 B2 | 10/2006 | Kelling | |
| 8,123,520 B2 | 2/2012 | Yamamoto et al. | |
| 8,133,054 B2 | 3/2012 | Yamamoto et al. | |
| 8,152,521 B2 | 4/2012 | Yamamoto et al. | |
| 2007/0065768 A1 | 3/2007 | Nadav | |
| 2008/0227046 A1 | 9/2008 | Lowe et al. | |
| 2009/0042159 A1 * | 2/2009 | Yamamoto | A61C 7/00 433/18 |
| 2009/0061375 A1 * | 3/2009 | Yamamoto | A61C 7/00 433/6 |
| 2009/0061379 A1 * | 3/2009 | Yamamoto | A61C 7/00 433/24 |
| 2009/0061380 A1 * | 3/2009 | Yamamoto | A61C 7/00 433/24 |
| 2010/0055634 A1 * | 3/2010 | Spaulding | A61C 7/00 433/5 |
| 2010/0092916 A1 | 4/2010 | Teixeira et al. | |
| 2011/0136070 A1 | 6/2011 | Rubin et al. | |
| 2011/0269095 A1 | 11/2011 | Singh | |
| 2012/0040300 A1 * | 2/2012 | Levens | A61C 1/07 433/5 |
| 2012/0094246 A1 * | 4/2012 | Pavlin | A61C 7/08 433/6 |
| 2012/0322018 A1 * | 12/2012 | Lowe | A61C 7/00 433/6 |
| 2013/0059263 A1 * | 3/2013 | Lowe | A61C 7/00 433/6 |
| 2013/0323669 A1 * | 12/2013 | Lowe | A61C 7/00 433/24 |
| 2014/0023983 A1 * | 1/2014 | Lowe | A61C 7/006 433/24 |
| 2014/0335467 A1 * | 11/2014 | Yamamoto | A61C 7/008 433/6 |
| 2015/0079533 A1 * | 3/2015 | Lowe | A61C 7/00 433/24 |
| 2016/0184054 A1 * | 6/2016 | Lowe | A61C 7/008 433/24 |

FOREIGN PATENT DOCUMENTS

| | | |
|---|---|---|
| WO | 2008/065761 | 6/2008 |
| WO | 2009/048086 | 4/2009 |
| WO | 2009/123965 | 10/2009 |

OTHER PUBLICATIONS

Hirashita et al., "Ha wa Ugoku-Kyousei Shikarinshou no Seibutsugakuteki Haikei (Tooth Moves-Biological Background in Clinical Orthodontics)", Ishiyaku Publishers, Inc., 1st ed., 2006, pp. 2-4, 12, 26-27.

Ohmae et al., "Biomechanical acceleration of experimental tooth movement by ultrasonic vibration", Orthod. Waves, 60(4), 2001, pp. 201-212.

Oates et al., "Pulsating forced in orthodontic treatment", Am. J. Orthod., vol. 74, No. 5, Nov. 1978, pp. 577-586.

Kopher et al., "Suture Growth Modulated by the Oscillatory Component of Micromechanical Strain", Journal of Bone and Mineral Research, vol. 18, No. 3, Nov. 3, 2003, pp. 521-528.

Fujita et al., "Ha no Kaibogaku (Anatomy of Teeth)", Textbook of Dental Anatomy, 22nd Edition, 1995, PP.

Shimizu, "A study of the movement of the lateral incisor of the macaca fuscata loaded by a vibrating force", Journal of the Japanese Orthodontic Society, 45, 1986, pp. 56-72.

Search report from PCT/JP2013/006194, dated Nov. 26, 2013.

U.S. Appl. No. 60/234530 to Mao, filed Sep. 22, 2000.

* cited by examiner

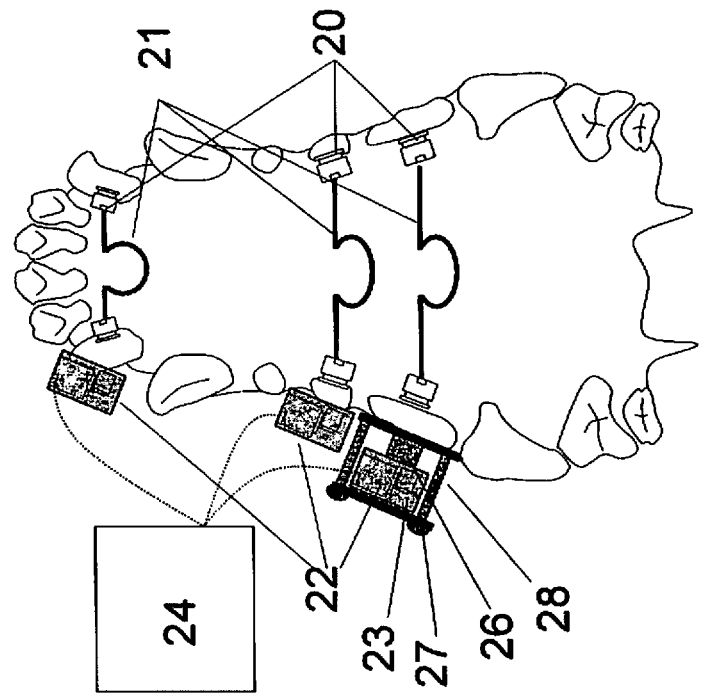
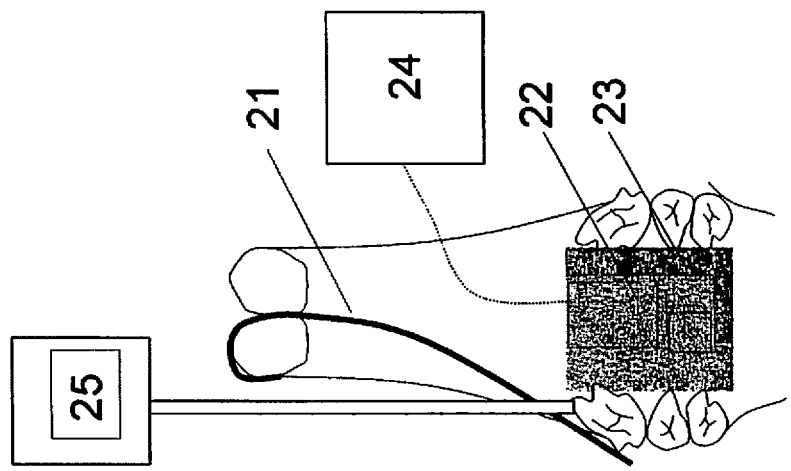

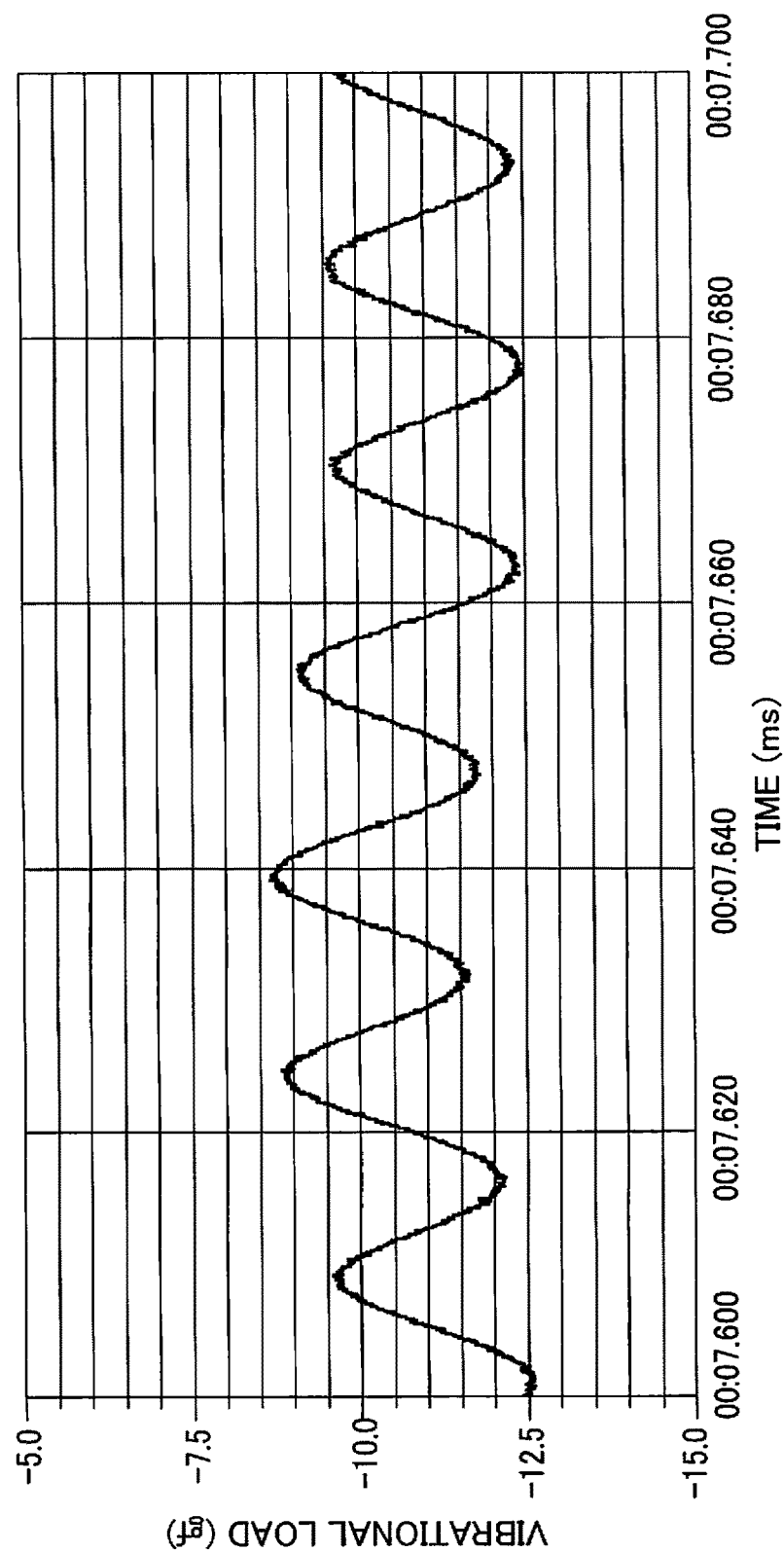

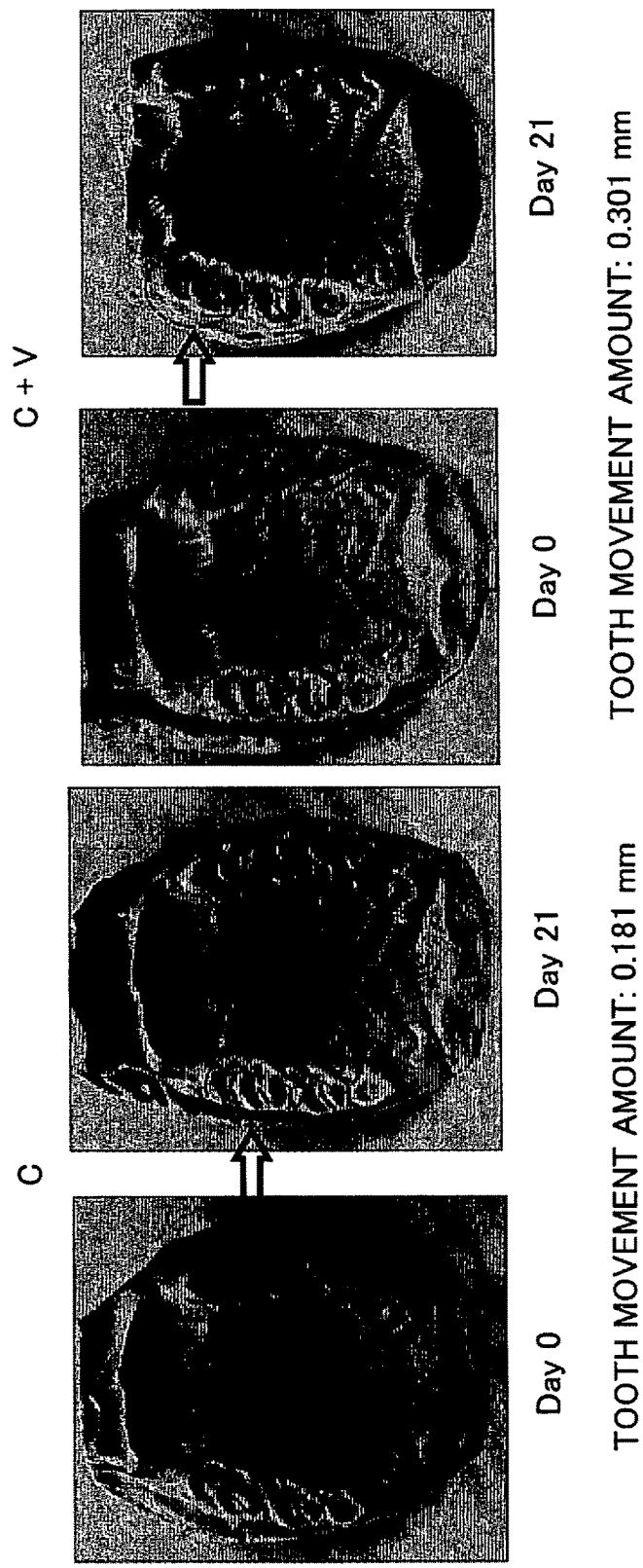

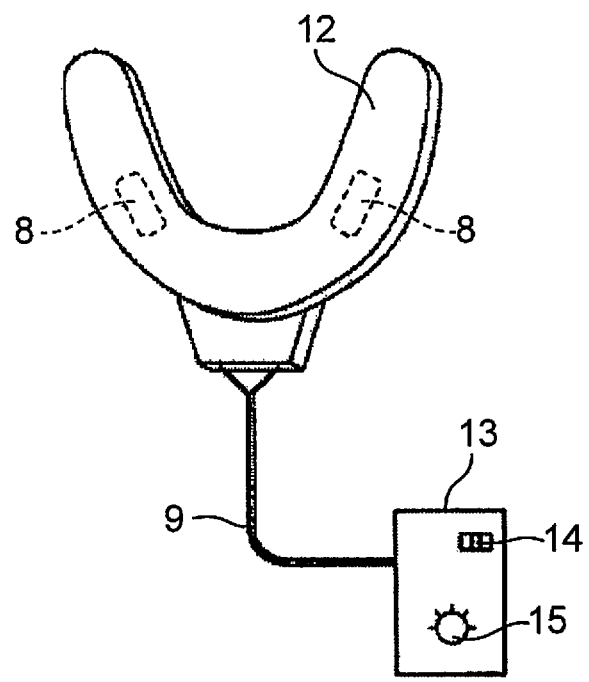

FIG.20

| TYPE OF TEETH | CROWN LENGTH | CROWN WIDTH | TOOTH LENGTH | VOLUME | SURFACE AREA | VOLUME RATIO | SURFACE AREA RATIO | $M_1$ | $m_2$ | k | $c_1$ | $c_2$ | DISPLACEMENT |
|---|---|---|---|---|---|---|---|---|---|---|---|---|---|
| | mm | mm | mm | mm$^3$ | mm$^2$ | | | g | kg | N/m | Ns/m | Ns/m | μm |
| UPPER CENTRAL INCISORS | 7.2 | 8.6 | 23.8 | 1,473.7 | 129.5 | - | - | 2.9 | 2.0 | 1000000.0 | 63.0 | 980.0 | - |
| UPPER FIRST MOLARS | 11.8 | 10.6 | 19.2 | 2,401.5 | 179.3 | 1.63 | 1.38 | 5.0 | 2.0 | 1384801.3 | 87.2 | 1357.1 | 0.04 |

VALUES FROM NON-PATENT LITERATURE 5

VALUES FROM NON-PATENT LITERATURE 7

DENTAL VIBRATION APPLICATION METHOD AND DENTAL VIBRATION APPLICATION DEVICE

TECHNICAL FIELD

The present invention relates to a dental vibration application method and a dental vibration applicator.

BACKGROUND ART

Orthodontic treatment is treatment in which a mechanical force (orthodontic force) is applied to the teeth for improvement of teeth alignment.

Non-Patent Document 1 provides detailed descriptions about the principle of the tooth movement.

With regard to the tooth movement in the orthodontic treatment, the periodontal ligament plays important roles as responding tissues to a mechanical force generated by an orthodontic appliance.

The periodontal ligament is fibrous tissues having a width of about 0.2 mm, the fibrous tissues being interposed between the alveolar bone and the cementum covering a surface layer of the root. The periodontal ligament is composed of various cells such as the periodontal ligament fibroblasts, osteoblasts, osteoclasts, cementoblasts, Malassez' epithelial rest cells, macrophages and vascular endothelial cells.

Under physiological conditions, the periodontal ligament is important for supporting teeth, sensory reception, supplying nutrients by the vascular plexus, and maintaining and regenerating the periodontal tissues. The periodontal ligament also has a role as a buffer zone which protects the teeth and circumjacent tissues from mechanical stimulation such as a chewing force and occlusal force.

Different types of mechanical stimulation in tension and compression forces are transmitted to the periodontal ligament and the alveolar bone of the teeth, to which an orthodontic force is applied, to cause histologically different regions in the tension and compression sides. In the tension side, the periodontal ligament stretched to expand a periodontal ligament space. Subsequently, as a result of apposition of bone promoted by the osteoblasts in a surface layer of the alveolar bone, the expanded periodontal ligament space returns to a width comparable to that under the physiological state. On the other hand, in the compression side, the root gets closer to the alveolar bone so that compression of the periodontal ligament and a narrowed periodontal ligament space are observed. Bone resorption is then promoted by osteoclasts in the compression side.

In this manner, the alveolar bone changes in shape during the tooth movement as a result of bone resorption on compression side primarily happening to the anterior alveolar bone of the moving tooth and formation of bone primarily happening to the posterior alveolar bone.

Multi-bracket appliances and orthodontic mouthpieces are currently used as orthodontic therapeutic appliances. These appliances use a return force of bent wires or deformed elastomer materials to give a continuous force to the teeth.

However, the orthodontic treatment using the continuous force requires for the orthodontic appliances to be always attached to the teeth throughout a treatment period which is several years. This means a considerable physical and psychological burden on patients.

Application of a dynamic load such as vibration instead of a continuous force is considered as one of effective methods to shorten an orthodontic treatment period. There have been researches conducted previously.

Non-Patent Document 2 (1978) describes a comparison between a case of applying a continuous force of 69.3 gf to the left upper canine teeth of German shepherds using a coil spring and a case of applying an intermittent force to the upper right canine teeth, the magnitude of the intermittent force being controlled by using a similar coil spring and a pulse generator. With regard to the intermittent force application, 17 seconds for applying a force of 66.0 gf and 3 seconds for applying no force are repeated for the first 6 days, and then 17 seconds for applying a force of 49 gf and 3 seconds for applying no force are repeated in the next 6 days. It was reported that the upper right canine, to which the intermittent force had been applied, showed a greater increase in a movement amount after 12 days.

Non-Patent Document 3 (1986) describes a comparison in Japanese macaques between the upper left lateral incisors, to which vibrational stimulation were applied for 1.5 hours per day at a maximum load of 40 gf, average load of 25 gf, load amplitude of ±15 gf and frequency of 115 Hz to 140 Hz, and the upper right lateral incisors, to which a continuous force of 40 gf were applied. Consequently, it was reported that the upper left lateral incisors had shown a greater increase in a tooth movement amount after 3 weeks.

Although these Non-Patent Documents 2 and 3 show effects on shortened orthodontic treatment under the application of vibrational stimulation, application to humans is impractical since a large vibration generator is attached for a long period of time and vibration having a large load are continuously applied.

Non-Patent Document 4 (2001) shows a comparison of a movement amount between the upper second bicuspids of the same beagle dog. One of the upper second bicuspids was subjected to a continuous force of 80 gf in addition to high-frequency vibrational stimulation at the amplitude of 100 μm and frequency of 28.069 kHz for 2 minutes once every 2 weeks whereas the other of the second bicuspids on the opposite side was subjected only to a continuous force of 80 gf. Consequently, it was reported that there had been a greater tooth movement amount if the continuous force was combined with the high-frequency vibrational stimulation than if only the continuous force is used.

Non-Patent Document 5 shows a study about viscoelastic characteristics of human periodontal tissues, and provides a model of a dynamic system composed of the teeth, periodontal ligament and alveolar bone as shown in FIG. 1.

Non-Patent Document 6 (2003) reports that suture growth of rabbits in a growth period was promoted under an application of a periodic force at a frequency of 1 Hz to the cranial suture 10 minutes a day for 12 days, the periodic force having a maximum load as a compression force of 5 N. Since the load application did not aim at moving the teeth in a fixed direction through the periodontal ligament with viscoelasticity, the load was considerably larger than a load used for moving teeth in the field of orthodontic treatment. Although the maximum load and frequency are described, there are no disclosures about a size of the vibrational load.

Likewise, Patent Document 1 (2000) reports that the suture growth was promoted under applications of periodic forces at frequencies of 0.2, 0.4, 0.6, 0.8 or 1.0 Hz, each of which was applied 10 minutes a day for 12 days to the cranial sutures of rabbits, the periodic forces having maximum loads 5 N or 2 N. Like Non-Patent Literature 6, there are no disclosures about a size of the vibrational load although the maximum load and frequency are described.

The sutures are fibrous tissues, which join bones composing the neuro-cranium and facial cranium. The sutures are known to be a major site of the cranial growth. In short, the cranial growth is induced by differentiation of the mesenchymal cells existing in the sutures into the osteoblasts through the osteoblast precursor cells, the osteoblasts adding the new bone to the suture borders.

Due to progression of the bone addition, all sutures eventually change over to the synostosis. In humans, the frontal suture closes one year after birth whereas other sutures further gradually change over to the synostosis during adulthood. In this regard, it is expected that there are differences from the periodontal ligament, which maintains homeostasis as fibrous tissue through the life without calcification.

In addition to their roles in the cranial growth, the sutures also have a role of receiving mechanical stimulation in the neuro-cranium and facial cranium. With regard to orthodontic treatment, patients during the growth period having skeletal discrepancy of the maxillofacial region are treated by applying mechanical stimulation to the sutures as a maxillary orthopedic force. It is observed that there are an increase in a suture width, acceleration of cell proliferation, increased extracellular matrix production and calcification at borders with bone as a result of applying a tension force to the sutures. This implies that bone formation is promoted by an application of the tension force. On the other hand, it is expected that growth at the sutures is inhibited by application of a compression force to the sutures. In a recent report, an application of a compression force to the sutures results in activation of osteoclasts and bone resorption which in turn leads to compression of the sutures and inhibits bone growth.

When mechanical force is applied to the teeth, a tension side and a compression side are simultaneously observed in the alveolar bone in correspondence to a stimulation direction, so that each of bone resorption and bone formation progresses in each side. On the other hand, tissue reactions in the sutures loaded by one of tension force and compression force cause one of bone formation and bone resorption around the sutures subjected to the stimulation. In this manner, there are different dynamics between the periodontal ligament and the sutures under mechanical stimulation. Therefore, the vibration parameters such as a load or application period cannot be directly applied to orthodontic treatment since mechanism of action under an application of vibration to the periodontal ligament is different from application of vibration to the sutures described in Non-Patent Documents 1 and 6.

A device configured to apply vibration to dentition when a user bites the planar device to which a vibrator is connected is known as an attempt of a practical device for applying vibration to the teeth (c.f. Patent Document 2). There is another device which applies a pulsed load to the entire dentition when a mouthpiece with an embedded metal wire is attached, the mouthpiece being connected to an extra-oral transducer (c.f. Patent Document 3). There is another device including a metal orthosis ring, which is attached to an individual tooth, and an extra-oral transducer, which is connected to the metal band, the device applying a pulsed load to an arbitrary tooth fitted with the orthosis (c.f. Patent Literature 4). However, the object of Patent Document 2 is to promote gingival circulation and alleviate pain accompanying orthodontic treatment. Patent Document 2 does not describe how to shorten an orthodontic treatment period. In addition, although a period of 10 minutes to 15 minutes is disclosed as one of the parameters of vibration application period, there are no experimental data as grounds and no specific descriptions about a size of the vibrational load. Although the objects of Patent Documents 3 and 4 are to shorten an orthodontic treatment period, like the present invention, there are no specific descriptions about vibration characteristics.

There are also devices of a bite plate type, which are used for the purpose of shortening an orthodontic treatment period, with description about their vibration characteristics (Patent Documents 5, 6 and 7).

Non-Patent Literature 5 proposes a device which applies vibrations at 0.1 Hz to 40 Hz having a maximum load of 0.1 N to 10 N on the basis of experimental data in rabbits. However, these values are based on the experimental data in which suture growth was promoted under an application of vibrational stimulation to rabbit cranium. Non-Patent Literature 5 discloses experimental data under applications of compression forces with maximum loads of 2 N and 5 N but there is no description about other vibration characteristics. In addition, there is no experimental data about tooth movement through the periodontal ligament.

Patent Documents 6 and 7 propose devices configured to apply vibrations of 0.1 N to 10 N at 0.1 Hz to 1200 Hz for 1 minute to 60 minutes. Patent Document 8 proposes a device configured to apply vibrations of 0.01 N to 3 N at 0.1 Hz to 1000 Hz. These documents reveal vibration characteristics and device structures but do not disclose any data as grounds.

Patent Document

Patent Document 1: U.S. Provisional Application No. 60/234,530
Patent Document 2: U.S. Pat. No. 5,967,784
Patent Document 3: U.S. Pat. No. 4,123,844
Patent Document 4: U.S. Pat. No. 4,229,165
Patent Document 5: U.S. Pat. No. 6,832,912
Patent Document 6: WO 2009/123965
Patent Document 7: U.S. Unexamined Patent Publication No. 2011-136070
Patent Document 8: WO 2009-048086

Non Patent Document

Non-Patent Literature 1: Ayao Hirashita and Teruko Yamamoto: Ha wa Ugoku (Tooth Movement), Ishiyaku Publishers, Inc., 2006
Non-Patent Literature 2: J. C. Oates, R. N. Moore and A. A. Caputo: Pulsating forces in orthodontic treatment, American Journal of Orthodontics, 74(5), 577-586, 1978
Non-Patent Literature 3: Yoshiyuki Shimizu: A study of the movement of the lateral incisor of the macaca fuscata loaded by a vibrating force, Journal of the Japanese Orthodontic Society, 45(1), 56-72, 1986
Non-Patent Literature 4: Masami Ohmae, Shigeru Saito, Tomio Morohashi, Qu Hong, Kenji Seki, Hitomi Kurabayashi, Kenichi Yamasaki, Shoji Yamada, Tomohiro Okano and Yoshinobu Shibasaki: Biomechanical acceleration of experimental tooth movement by ultrasonic vibration in vivo: Part 1 Homo-directional application of ultrasonication to orthodontic force, Orthod. Waves, 60(4), 201-212, 2001
Non-Patent Literature 5: D. H. Noyes and C. W. Solt: Measurement of mechanical mobility of human incisors with sinusoidal forces, Journal of Biomechanics, 6, 439-442, 1973

Non-Patent Literature 6: R. A. Kopher and J. J. Mao: Suture growth modulated by the oscillatory component of micromechanical strain, Journal of Bone and Mineral Research, 18(3), 521-528, 2003

Non-Patent Literature 7: Tsunetaro Fujita, Tadao Kirino and Yasuo Yamashita: Ha no Kaibogaku (Anatomy of Teeth), Kanehara & Co., LTD., 1995

SUMMARY OF INVENTION

With regard to a range of vibration characteristics for shortening an orthodontic treatment period, the aforementioned background arts require long stimulation in excess of 1 hour or give a large compression force of 2 N or 5 N as a maximum load. Therefore, there is a very great burden on patients. The aforementioned documents do not describe an amount of deformation which the periodontal ligament receives from vibrational stimulation and how many times the periodontal ligament receives the vibrational stimulation, the periodontal ligament working as an important role for the tooth movement.

The present invention is to solve the aforementioned problems. The object of the present invention is to specify an effective range of vibration characteristics for shortening a treatment period, and to provide a dental vibration applicator and dental vibration application method for reducing a burden on a patient.

The vibration application method according to one aspect of the present invention includes steps of contacting a contact portion with at least one of teeth, and vibrating the contact portion so as to give the contact portion displacement of no less than 0.04 μm.

The dental vibration applicator according to another aspect of the present invention has a contacting instrument including a contact portion which contacts at least one of teeth or an orthodontic appliance that is attached for orthodontic treatment of the at least one of the teeth, and a vibration generator configured to vibrate the contact portion. The contact portion is displaced by no less than 0.04 μm during vibration caused by the vibration generator.

According to the method and device of the present invention, a period of orthodontic treatment may be shortened by specifying an effective range of vibration characteristics for shortening a treatment period and applying an appropriate vibrational stimulation to a patient to activate metabolism of the periodontal ligament and alveolar bone.

The object, characteristics and advantages of the present invention will be made clear by the following detailed description and attached drawings.

BRIEF DESCRIPTION OF DRAWINGS

FIG. 3A is a schematic view of an experimental system using rats.

FIG. 3B is a schematic view of an experimental system using beagles.

FIG. 4 is a graph of a vibrational load waveform of a vibration device used in an experiment.

FIG. 5 shows comparative photographs of a tooth movement amount in an experiment using rats.

FIG. 14 is a perspective view of a bite plate-type vibration application device according to the fourth embodiment.

FIG. 20 is a table of estimated results for displacement of upper first molars under application of vibrations of 3 gf and 100 Hz.

DESCRIPTION OF EMBODIMENTS

<Problems which Prior Arts Face>

Figure 1:
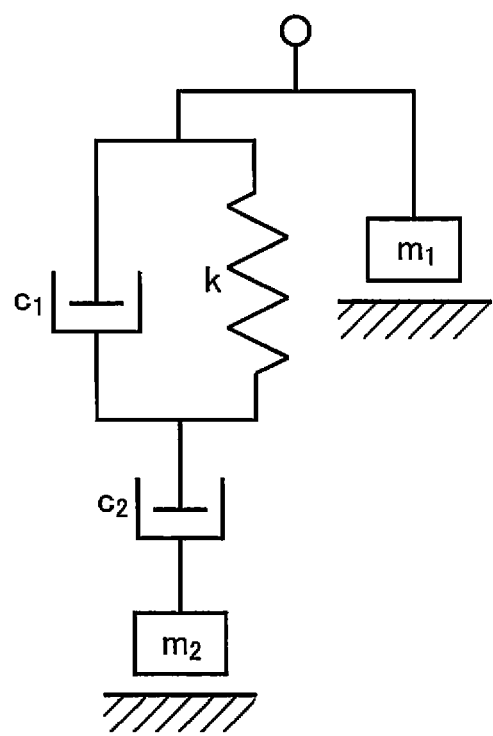
FIG. 1 is a schematic view of a model of a dynamic system composed of the human teeth, periodontal ligament and alveolar bone.

The aforementioned Patent Document 4 proposes technologies for increasing a tooth movement amount by applying high-frequency vibration. However, it is expected that such high-frequency compulsory vibration cannot give the periodontal ligament stimulation efficiently. The reason is shown in the following description which uses a dynamic model proposed in Non-Patent Document 5 (c.f. FIG. 1).

The mass element $m_1$ represents a weight of a tooth. The mass element $m_2$ represents a weight of a teeth root portion such as the alveolar bone, maxilla or mandible which supports the tooth. The elasticity element k represents the elasticity of the periodontal ligament. The viscosity element $c_1$ represents the viscosity of the periodontal ligament. The viscosity element $c_2$ represents the viscosity of the root portion.

In Non-Patent Document 5, representative parameters of the upper central incisor in humans are reported as $m_1=2.9$ g, $m_2=2.0\times10^3$ g, $k=1.0\times10^6$ N/m, $c_1=63.0$ Ns/m and $c_2=980.0$ Ns/m.

Figure 2:
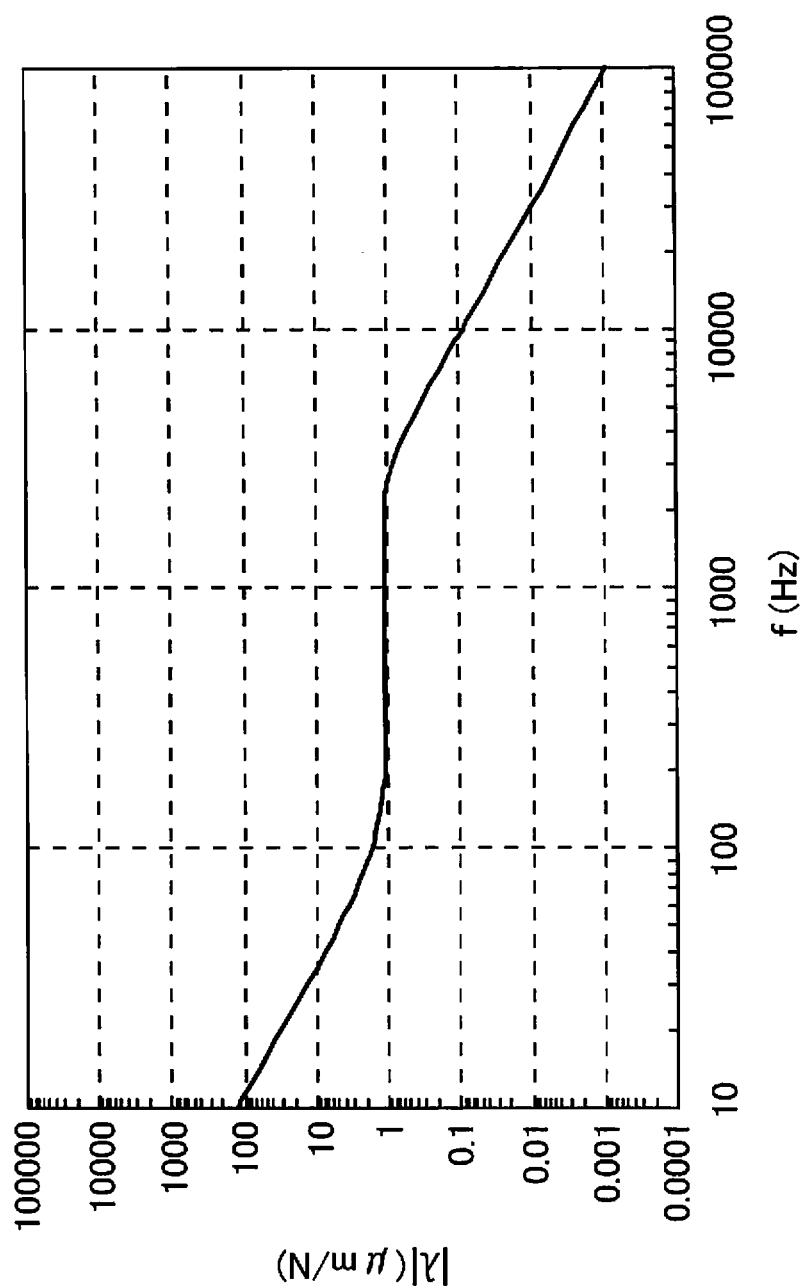
FIG. 2 is a graph showing a relationship between a ratio of load to displacement and a frequency of compulsory vibration.

FIG. 2 shows an analysis result about vibration under application of compulsory vibration to the upper incisors, the analysis result relying on the report of Non-Patent Document 5. In FIG. 2, $\lambda$ indicates a ratio of F (N) to displacement X (μm), where F(N) represents the difference between maximum and minimum values of a vibrational load. f (Hz) indicates frequency. When the vibrational load is explained with some numeral value in the following description, the value means the difference between maximum and minimum values of a resultant vibration waveform.

It is figured out from FIG. 2 that tooth displacement per applied vibrational load becomes very small if a frequency is several kHz or higher. For example, in contrast to $|\lambda|=1.68$ μm/N at a frequency of 100 Hz, the value becomes small as $|\lambda|=0.011$ μm/N at a frequency of 28 kHz. On the basis of these values, a vibrational load of 3.6 N or more is required at the frequency of 28 kHz to obtain displacement of 0.04 μM, in contrast to the vibrational load of 0.03 N or more at the frequency of 100 Hz.

The relationship is valid even when the mass elements $m_1$, $m_2$, the elasticity element k and the viscosity elements $c_1$, $c_2$ are comparatively large, like molar teeth. For example, the periodontal tissue may be considered, where $m_1$, $m_2$, k, $c_1$ and $c_2$ are all equal to 1.5 times as large as the parameters about the upper incisors. Namely, $m_1=4.4$ g, $m_2=3.0$ kg, $k=1.5\times10^6$ N/m, $c_1=94.5$ Ns/m and $c_2=1470.0$ Ns/m. The tooth displacement per applied vibrational load becomes $|\lambda|=1.12$ μm/N at the frequency of 100 Hz whereas the tooth displacement per applied vibrational load becomes very small as $|\lambda|=0.007$ μm/N at the frequency of 28 kHz. On the basis of these values, 0.04 N or more of the vibrational load is required to obtain displacement of 0.04 μm under the frequency of 100 Hz whereas 5.8 N or more of the vibrational load is required under the frequency of 28 kHz.

Without tooth deformation, it is expected that the aforementioned tooth displacement is equivalent to deformation of the periodontal ligament. Accordingly, it is also expected that deformation of the periodontal ligament becomes small at high frequencies.

Therefore, a much larger vibrational load is required under high-frequency vibration than low-frequency vibration to give the periodontal ligament a fixed amount or more of deformation.

However, it is necessary to devise safety measures such as treatment with water injection since an increase in energy given to the body causes a larger temperature rise in body tissues as a vibrational load becomes larger.

First Embodiment

Verification of vibrational stimulation characteristics by the present inventors are described in the context of the first embodiment. Various technologies for resolving the aforementioned problems become clear from the following verification.

The present inventors used the following method to verify vibrational stimulation characteristics, from which the aforementioned effects of shortening an orthodontic treatment period are obtained.

Male Wistar rats age 22 weeks or older and male beagle dogs age 10 months or older were used to verify the vibrational stimulation characteristics. Schematic views of experimental systems are shown in FIGS. 3A and 3B. FIG. 3A is a schematic view of an experimental system using the rats whereas FIG. 3B is a schematic view of another experimental system using the beagle dogs.

In the experiment using the rats, the present inventors fabricated a device including an orthodontic wire 21 and placed the device in all the rats so that the device applied a continuous force of 15 gf to the upper right first premolar to cause tooth movement.

A vibration motor 22 having a tungsten eccentric weight (φ4×2 mm) attached to a DC motor (Model KHN4NZ1R, Minebea Co., Ltd.) was used to apply vibration to the dentition. The vibration motor 22 was placed in an ABS plastic case 23 to prevent rotation of the motor from being interfered with the periodontal tissue or the tongue. The vibration motor 22 was firmly immobilized with a ligature wire to the occlusal surface of the maxilla so that motor vibration becomes coincident to vibration of target teeth for movement. A vibrational load was measured by a rod-shaped load cell 25 (Model LTS-500GA, Kyowa Electronic Instruments Co., Ltd.). The distal end of the rod was pressed against an upper portion of the mesial side of the upper first premolar so that an angle with the palate was 45 degrees in order to measure the vibrational load. The reference symbol 24 represents a power supply.

With regard to tooth movement method in the experiment using the beagle dogs, the present inventors attached an orthodontic bracket 20 to the upper left and right third incisors, second bicuspids and third bicuspids, and fabricated a device including the orthodontic wire 21. The present inventors placed the device so that the device applied a continuous force of 50 gf to the third incisors in the direction of the palate side whereas the device applied a continuous force of 100 gf to the second bicuspids and third bicuspids.

The same vibration motor 22 as what had been used in the rat experiment was adhesively fixed to the buccal side of the teeth targeted for movement with light-polymerized resin for vibration application to the dentition. Vibrational load was measured by a coin-shaped load cell 26 (Model LMA-A-5N, Kyowa Electronic Instruments Co., Ltd.). The coin-shaped load cell 26 was immobilized between the eccentric vibration motor 22 and the teeth with a fixture including a mounting plate 27 and mounting screws 28 in order to measure a vibrational load applied to the teeth.

FIG. 4 is graph of a vibrational load waveform when vibration was applied to the rats. The difference between the maximum and minimum values of the resultant load was 3 gf.

Figure 6:
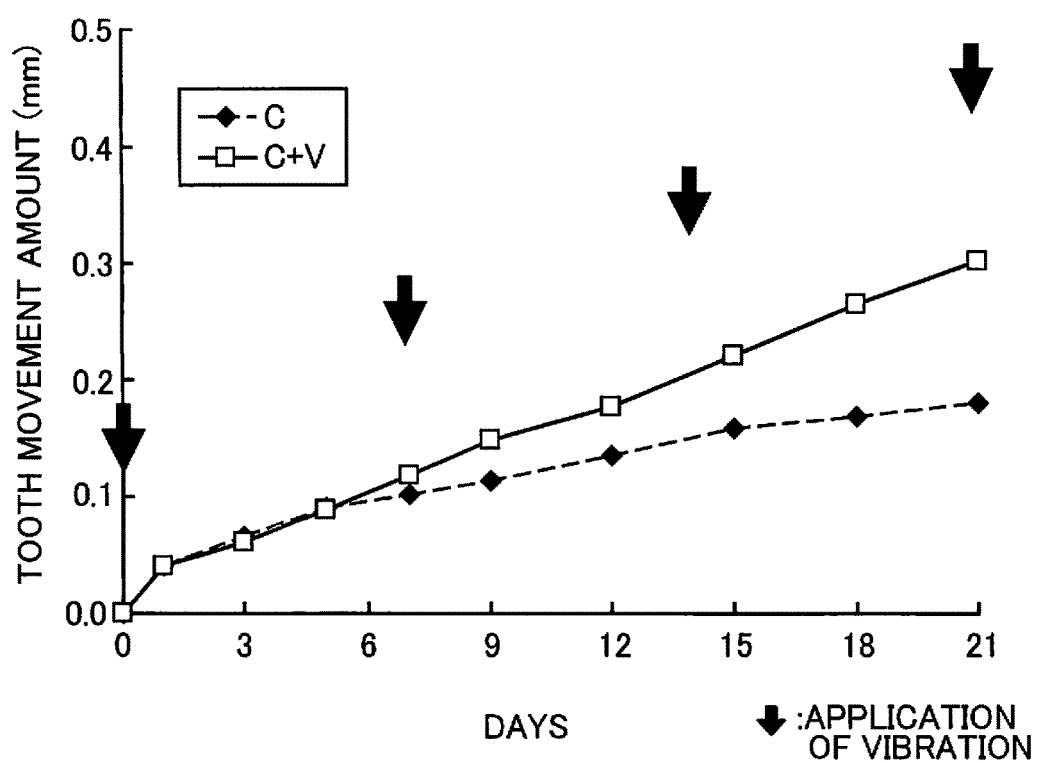
FIG. 6 is a graph of progressive changes in a tooth movement amount in an experiment using rats.
Figure 7:
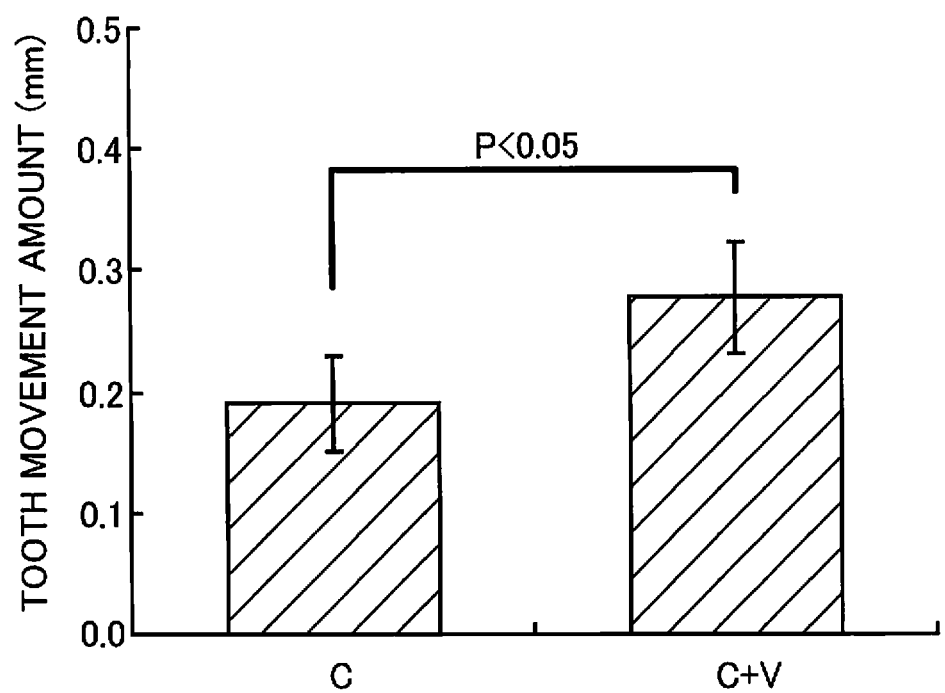
FIG. 7 shows a comparison of tooth movement amounts after 12 days in an experiment using rats.

FIGS. 5, 6 and 7 indicate verification results about the effects of shortening a treatment period for the rats. The effects of shortening a treatment period was evaluated by comparing tooth movement amounts between the continuous force plus vibration application group (C+V, 5 animals), for which vibration had been applied at a load of 3 gf and wave number of 10800 once a week in addition to application of a continuous force with an orthodontic wire, and a continuous force only group (C, 5 animals), for which only a continuous force had been applied with an orthodontic wire. FIG. 5 shows an example of denture molds of the rats used in the experiment. The tooth movement amounts were evaluated from these denture molds.

FIG. 6 is a graph of tooth movement curves of the individuals shown in FIG. 5. A difference in the tooth movement amounts of both individuals became apparent after day 7 when the second round of vibration was applied. The tooth movement amount of the individuals in the continuous force only group after 21 days was 0.18 mm whereas the tooth movement amount of the individuals in the continuous force plus vibration application group was 0.30 mm. It took 12 days for the tooth of the individuals in the continuous force plus vibration application group to move by 0.20 mm whereas it took 21 days for the tooth of the individuals in the continuous force only group to move by 0.20 mm.

FIG. 7 is a graph which compares movement amounts after 12 days between the continuous force plus vibration application group and the continuous force only group. The movement amount increased significantly (Student's T test, $P<0.05$) in the continuous force plus vibration application group in comparison with the continuous force only group. The increase amount of the continuous force plus vibration application group was about 1.4 times as large as that of the continuous force only group.

Figure 8:
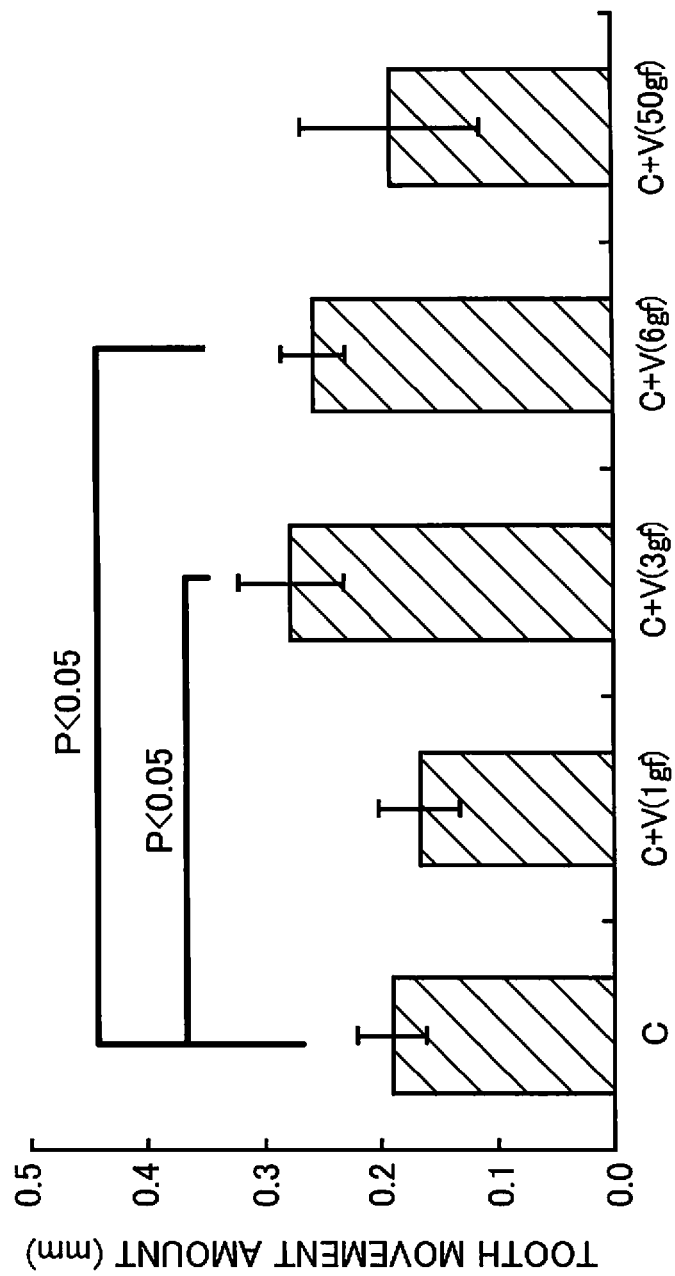
FIG. 8 is a graph showing a comparison of tooth movement amounts after 12 days in an experiment in which different vibrations in vibrational load are applied to rats.
Figure 9:
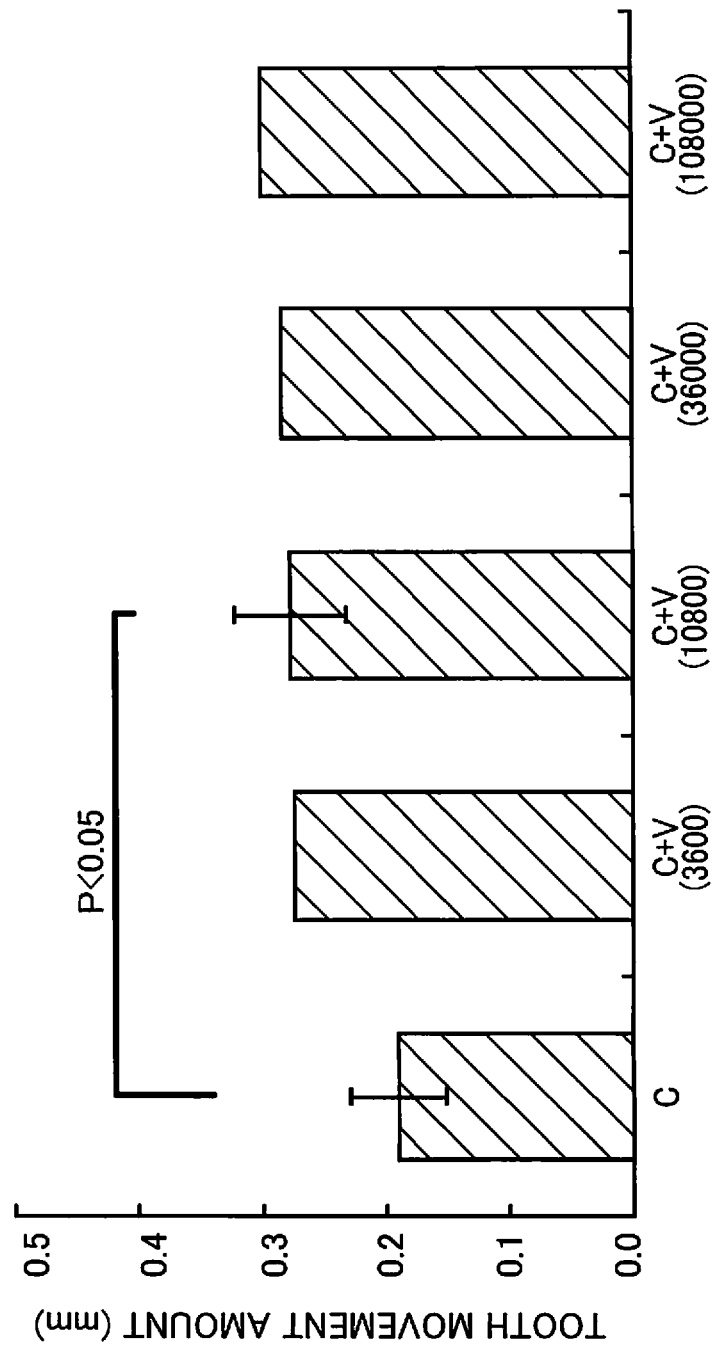
FIG. 9 is a graph showing a comparison of tooth movement amounts after 12 days in an experiment in which different vibrations in frequency are applied to rats.

FIGS. 8 and 9 show verification results of applying different vibrations in load and wave number about the effects of shortening a treatment period in the rats.

The effect of shortening a treatment period was evaluated by comparing movement amounts among the following groups (A) to (C).

(A) Continuous force plus vibration application group (C+V (1 gf), C+V (3 gf), C+V (6 gf), C+V (50 gf), four rats each), for which vibrations were applied at a load of 1 gf, 3 gf, 6 gf, 10 gf or 50 gf once a week, in addition to application of a continuous force with an orthodontic wire.

(B) Continuous force plus vibration application group (C+V (3600): 2 rats, C+V (10800): 4 rats, C+V (36000): 2 rats, CT+V (108000): 2 rats), for which vibrations were applied at a load of 3 gf and at a wave number of 3600, 10800, 36000 or 108000 once a week, in addition to application of a continuous force with an orthodontic wire.

(C) Continuous force only group (C, 4 rats), for which only a continuous force was applied with an orthodontic wire.

FIG. 8 is a graph comparing the tooth movement amounts after 12 days in an experiment in which different vibrations in load were applied. The tooth movement amounts in the groups, for which vibrations of 3 gf or 6 gf were applied in addition to a continuous force, respectively, increased significantly in comparison with the group subjected to a continuous force only (Student's T test, $P<0.05$). There were no significant differences in tooth movement amount between each of the groups, for which vibrations of 1 gf or 50 gf were applied, and the group subjected to a continuous force only.

FIG. 9 shows a comparison of the tooth movement amounts after 12 days in an experiment in which different vibrations in wave number were applied. All of the groups subjected to a continuous force and vibrations showed an increase trend of the tooth movement amount in comparison with the group subjected to a continuous force only. The tooth movement amount of the group, for which vibration having a wave number of 10800 were applied in addition to a continuous force, increased significantly in comparison with the continuous force only group (Student's T-test, $P<0.05$).

The effects of shortening a treatment period in the beagle dogs were evaluated by comparing tooth movement amounts of the following teeth (D) to (F) after 6 weeks.

(D) Teeth on the right side, to which vibrations at a load of 3 gf and wave number of 18000 were applied once every 2 weeks in addition to a continuous force with an orthodontic wire (C+V (3 gf)), five teeth.

(E) Teeth on the right side, to which vibrations at a load of 10 gf and wave number of 102000 was applied once a week in addition to a continuous force with an orthodontic wire (C+V (10 gf)), three teeth.

(F) Teeth on the left side to which only a continuous force was applied with an orthodontic wire (C), five teeth.

Figure 10:
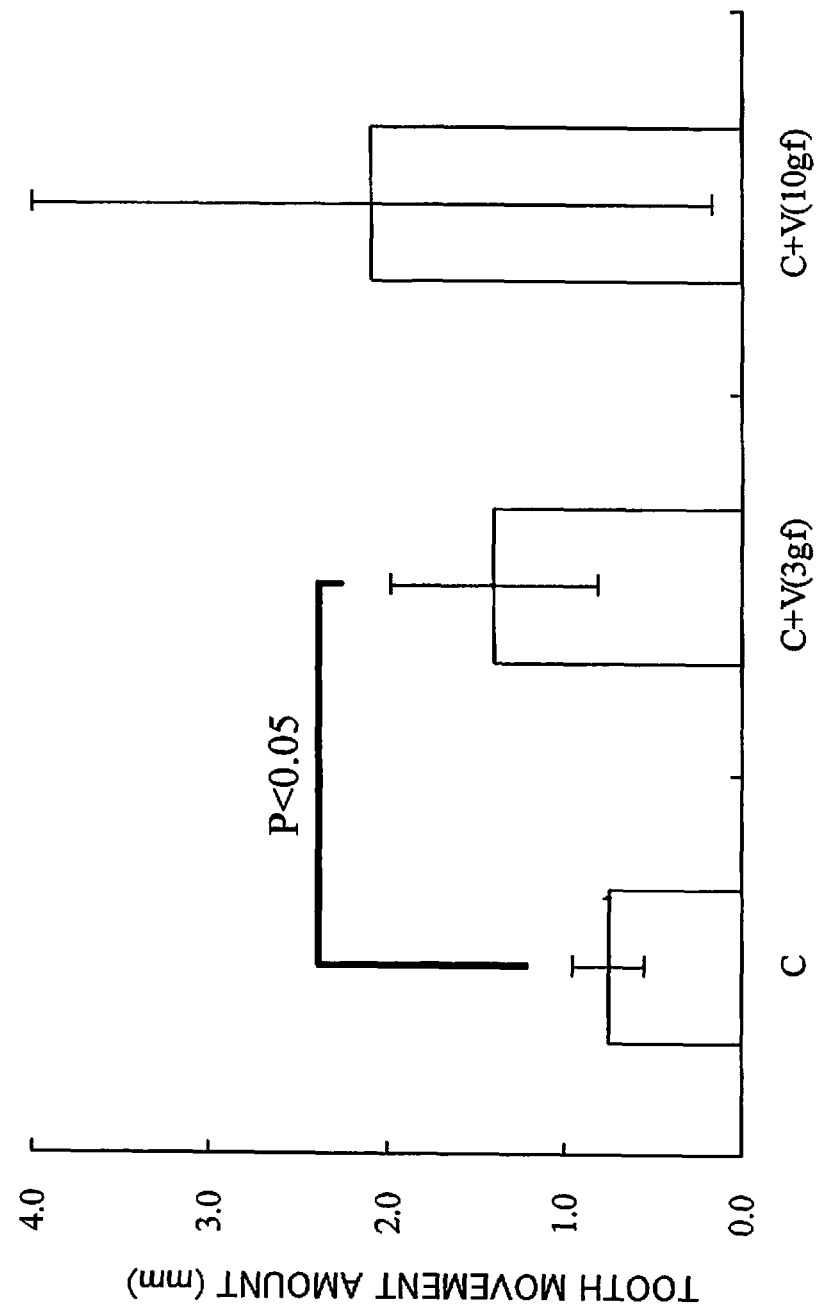
FIG. 10 is a graph showing a comparison of tooth movement amounts after 6 weeks in an experiment using beagle dogs.

FIG. 10 is a graph comparing the tooth movement amounts after 8 weeks.

The teeth, to which vibrations of 3 gf and 10 gf had been applied, respectively, showed an increase trend of the tooth movement amount in comparison with the teeth, to which only continuous force had been applied. The amount of the tooth movement, to which vibrations of 3 gf had been applied, increased significantly in comparison with the teeth subjected to a continuous force only (Student's T test, $P<0.05$).

Second Embodiment

A device used for shortening an orthodontic treatment period is described in the context of the second embodiment, the device including a vibration generator. The device applies vibration generated by the generator to the teeth or alveolar mucosa of a user.

The device used for shortening an orthodontic treatment period according to the present embodiment includes a vibration generator, a device (power supply) configured to supply power for the vibration generator, a controller, and a contacting instrument for transmitting the generated vibration.

Figure 11:
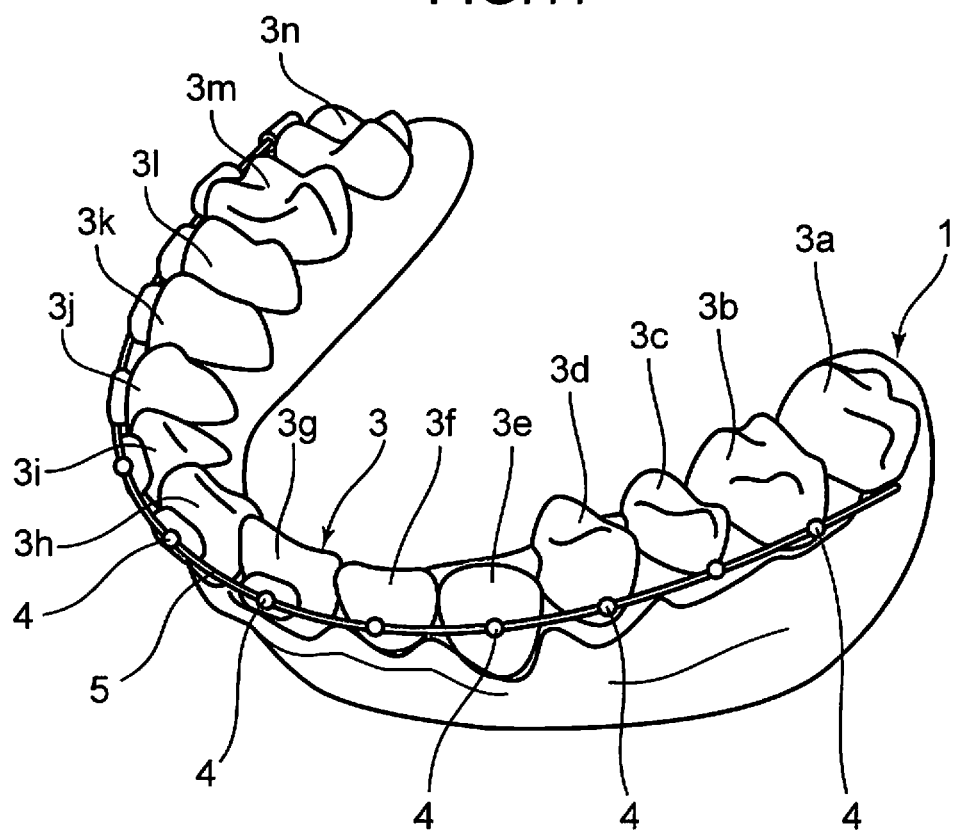
FIG. 11 is a perspective view of a mandibular dentition to which an orthodontic appliance is attached.

FIG. 11 is a perspective view of the mandibular dentition, to which an orthodontic appliance is attached. As shown in FIG. 11, each bracket 4 is fixed to the buccal surface of each of the teeth 3b to 3m of the dentition 3 (a to n) among the dentition and gingival tissue 1. A continuous wire 5 is engaged into each bracket 4. The dentition and occlusion may be treated with the orthodontic appliance by a continuous force applied to the dentition 3 due to a return force of the wire 5. The teeth, which fix the brackets 4, and the brackets 4, which are engaged with the wire 5, are not limited to those exemplified in FIG. 11.

Figure 12A:
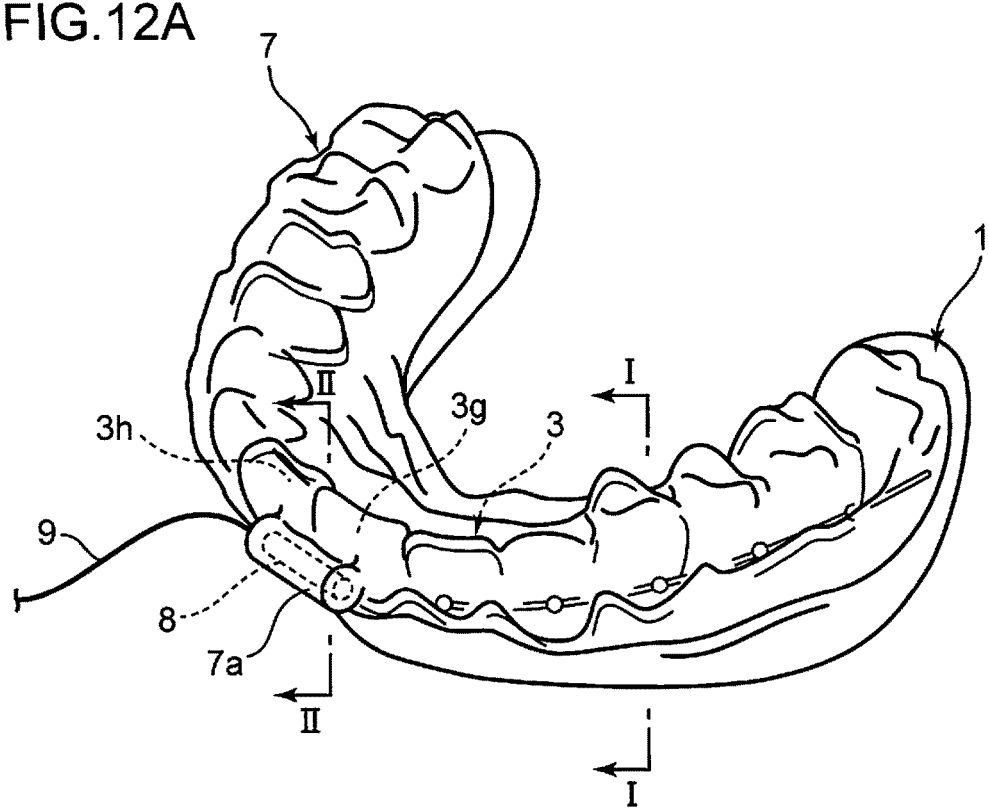
FIG. 12A is a perspective view of an exemplary mouthpiece-type vibration application device according to the second embodiment, the vibrational mouthpiece being attached to the dentition.
Figure 12B:
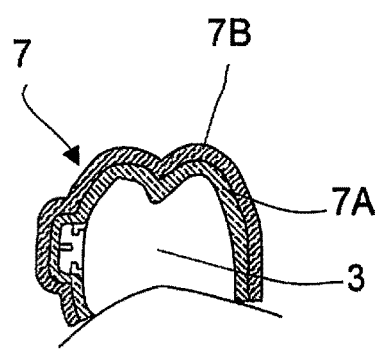
FIG. 12B is a cross-sectional view taken along line I-I shown in FIG. 12A.
Figure 12C:
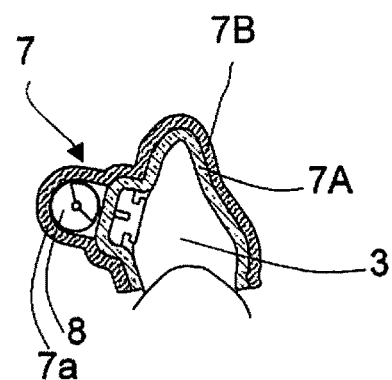
FIG. 12C is a cross-sectional view taken along line II-II shown in FIG. 12A.

FIGS. 12A to 12C indicate an embodiment of a mouthpiece-type device configured to apply vibration to the dentition 3 when a user attaches the device to the dentition.

FIG. 12A is a perspective view of the attached mouthpiece 7 which internally includes an electric motor (vibrator) 8. FIGS. 12B and 12C are cross-sectional views of FIG. 12A. As shown in FIG. 12A, the mouthpiece 7 according to the present embodiment is attached to the dentition 3, to which the aforementioned orthodontic appliance including the brackets 4 and the wire 5 is attached.

As shown in FIG. 12B, the mouthpiece 7 includes an inner mouthpiece 7A, which is placed directly over the dentition 3, and an outer mouthpiece 7B, which is externally placed over the inner mouthpiece 7A. Since the inner mouthpiece 7A contacts the dentition, the contact portion is exemplified by the inner mouthpiece 7A. The contacting instrument is exemplified by the mouthpiece 7. In the present embodiment, the mouthpiece 7 entirely covers the dentition. However, the principle of the present embodiment may be applied to a device configured to cover a single tooth. In the present embodiment, the inner mouthpiece 7A contacts the dentition through the orthodontic appliance. Alternatively, the inner mouthpiece 7A may contact the dentition directly.

The inner and outer mouthpieces 7A, 7B may be molded from an ordinary material for a mouthpiece, the material having ensured safety in terms of hygiene. For example, a sheet made of a polymer material such as ethylene vinyl acetate (EVA) resin may be suitably used for such a material. In this case, effects of allergies and alike are less likely to happen to the teeth and gingiva. The material is not limited to EVA. The EVA sheet is, however, preferable since the EVA sheet ensures electrical insulation and also functions as a heat insulator. The use of the EVA sheet for the inner mouthpiece 7A may result in softness of the inner mouthpiece 7A. Accordingly, damage may be less likely to happen to the teeth under orthodontic treatment since the EVA sheet absorbs high-speed components of mechanical vibration transmitted from the electric motor 8 (described later) to the teeth under orthodontic treatment.

There is an outward protrusion 7a on a front surface of the outer mouthpiece 7B, the protrusion 7a having an inner shape slightly larger than an outer shape of the electric motor 8 as an actuator. The compact and lightweight electric motor 8 is stored sideways in a void of the protrusion 7a (so that the vibrating direction is substantially perpendicular to the dentition 3). Vibration is transmitted to the mouthpiece under operation of the electric motor 8. On the basis of the learnings from the verification of the first embodiment, the power of the electric motor 8 may be adjusted so that the inner mouthpiece 7A is displaced by 0.04 μm or more. In the present embodiment, the vibration generator is exemplified by the electric motor 8.

For example, if an eccentric rotation motor used for a vibrator of a cellular telephone and alike is used as the electric motor 8, the electric motor 8 may cause vibration inexpensively. The vibration generator (electric motor 8) may be stored in the contacting instrument (mouthpiece 7). Alternatively, the vibration generator may be separate from the contacting instrument.

The inner mouthpiece 7A is placed over the inside of the outer mouthpiece 7B after the electric motor 8 is stored in the protrusion 7a. Under this state, the outer surface of the inner mouthpiece 7A is integrated in a watertight manner with the inner surface of the outer mouthpiece 7B so as to prevent saliva or rinsing water and alike from entering the protrusion 7a from the joining surfaces. Accordingly, there is little water entering the joining surface. If the electric motor 8 is a direct current (DC) motor, a power supply line 9 is led to the outside in an airtight manner through a through hole formed in the protrusion 7a of the outer mouthpiece 7B. The power supply line 9 is then led outside the mouth from the lips to be connected to a controller (such as a switch or motor speed control circuit) or power supply (such as a battery or other direct current (DC) power source). The power supply may be an alternating current (AC) power source if the electric motor 8 is an alternating current (AC) motor.

The mouthpiece 7 is attached as described above to apply vibration to the dentition 3 on which the orthodontic appliance (4 and 5) is mounted to apply a continuous force, so that the burden on the patient may be reduced, and the orthodontic treatment period may be shortened.

The mouthpiece 7 according to the present embodiment covers the dentition 3 entirely. Alternatively, a mouthpiece configured to only partially cover the dentition may be used as the contacting instrument.

Third Embodiment

The use of a mouthpiece described in the context of the second results in easy transmission of vibration to the teeth. However, it may be desired in orthodontic treatment to selectively transmit vibration to a specific tooth. Techniques which allow selective vibration transmission to a specific tooth are described in the third embodiment.

FIGS. 13A to 13D show an embodiment of a probe-type device which applies vibration to the dentition 3 when a user contacts the device with a tooth.

Figure 13A:
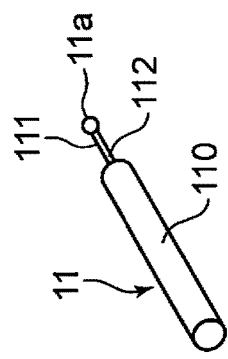
FIG. 13A is a perspective view of a probe-type vibration application device according to the third embodiment.

FIG. 13A is a schematic perspective view of a vibration generating probe 11. The vibration generating probe 11 includes a rod-shaped body 110 and an arm 111 which extends from an end surface of the body 110. A vibration generator (not shown) configured to generate vibration is stored in the body 110. The arm 111 includes a proximal end 112 connected to the body 110 and a ball-shaped probe head 11a. The probe head 11a is formed on the opposite side of the proximal end 112. Vibration generated by the vibration generator stored in the body 110 is transmitted to the probe head 11a through the arm 111. The probe head 11a is connected to the orthodontic appliance (4 and 5). Accordingly, the vibration is applied to the orthodontic appliance (4 and 5). In the present embodiment, the distal end is exemplified by the probe head 11a.

Figure 13B:
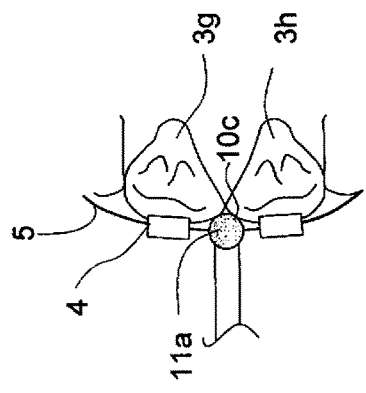
FIG. 13B is a side view of the probe-type vibration application device in use.
Figure 13C:
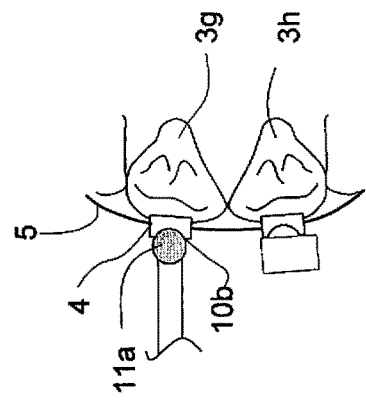
FIG. 13C is a side view of the probe-type vibration application device in use.

As shown in FIGS. 13B and 13C, the brackets 4 as the orthodontic appliance attached to the dentition 3 may have positioning portions for the probe head 11a. With the positioning portions, the probe head 11a may be contacted at the same position every time, so that vibration may be accurately applied to a target tooth. In FIG. 13B, a marking (colored mark) 10a is put on the brackets 4, the marking functioning as the positioning portions. The marking may be provided on the wire 5.

Figure 13D:
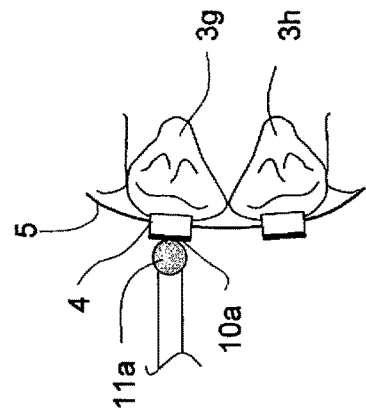
FIG. 13D is a side view of the probe-type vibration application device in use.

A depression 10b may be formed as the positioning portion in the brackets 4 as shown in FIG. 13C, instead of the marking 10a. The depression 10b is preferably coincident in shape with the probe head 11a. An indentation between the contact surfaces of a tooth 3g and a tooth 3h may be utilized as a depression 10c which functions as the positioning portion, as shown in FIG. 13D.

The probe head 11a may be composed from an elastic material. Accordingly, impact generated under vibration application may be alleviated.

When the probe head 11a of the vibration generating probe 11 is in contact with the dentition 3, to which the orthodontic appliance (4 and 5) is mounted to apply a continuous force, the burden on the patient is reduced, and the orthodontic treatment period may be shortened.

Fourth Embodiment

The mouthpiece described in the context of the second embodiment has to cover the dentition in order to be fixed in the oral cavity. If a device for transmitting vibration to teeth is easily fixed in the oral cavity, vibration application to the teeth becomes simplified. A device which is easily fixed in the oral cavity is described in the fourth embodiment.

FIG. 14 shows an embodiment of a bite plate-type device, which is fixed in the oral cavity when a user holds the device between the teeth, the device applying vibration to the dentition 3.

A bite plate 12 has a substantially U-shape. The electric motor 8 is stored in the bite plate 12. The electric motor 8 is electrically connected to a power supply 13, power switch 14 or volume adjuster 15 and alike which is placed outside the oral cavity. According to the present embodiment, vibration generated by the electric motor 8 may be applied to the dentition 3 by a user merely biting down on the bite plate 12.

When the bite plate 12 is occluded as described above by the dentition 3, to which the orthodontic appliance (4 and 5)

is mounted to apply a continuous force, the burden on the patient is reduced, and the orthodontic treatment period may be shortened.

The vibration generators and contacting instruments are exemplified by the mouthpiece 7, the vibration generating probe 11 and the bite plate 12. However, the vibration generators and contacting instruments are not limited to them.

Fifth Embodiment

Suitable contact between the contacting instrument and teeth is required in order to transmit vibration to the teeth. Techniques for easily obtaining suitable contact between the contacting instrument and the teeth are described in the fifth embodiment.

Figure 15:
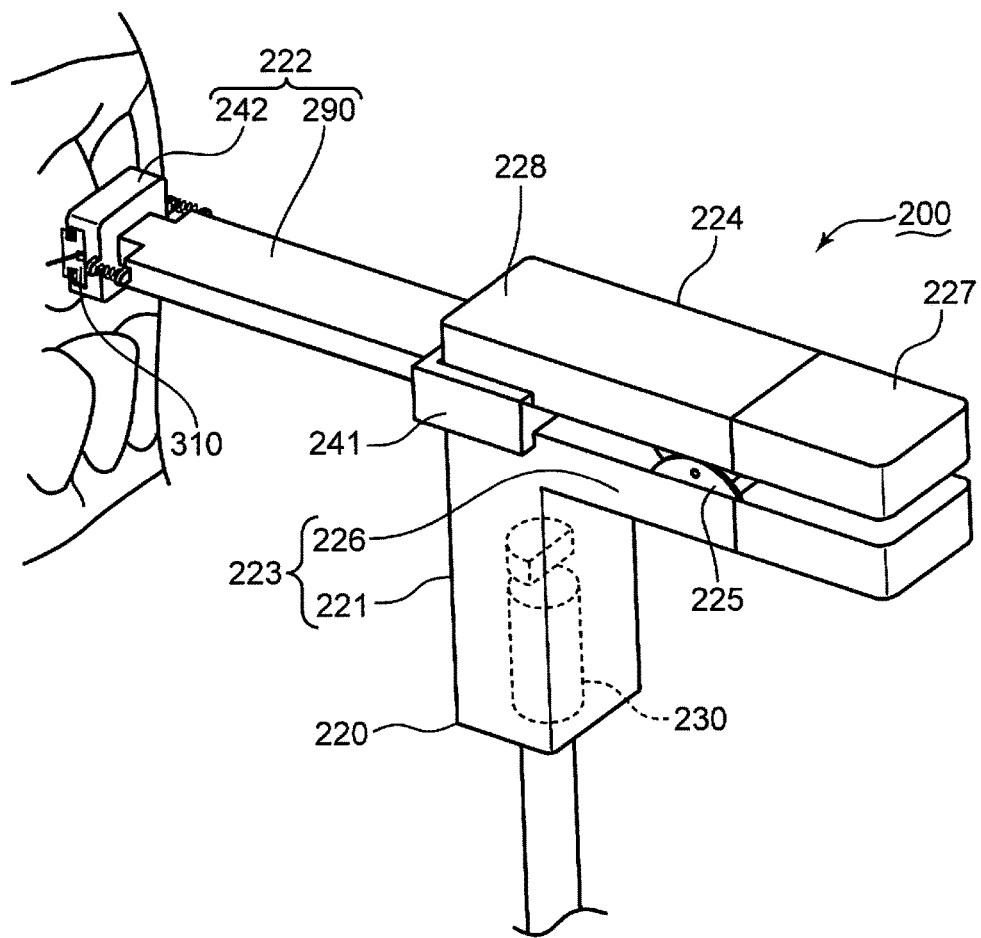
FIG. 15 is a schematic perspective view of an exemplary dental vibration applicator according to the fifth embodiment.

FIG. 15 is a schematic perspective view of an exemplary dental vibration applicator 200 according to the fifth embodiment. The dental vibration applicator 200 is described with reference to FIG. 15.

The dental vibration applicator 200 includes a vibration motor 230 and a housing 220. The vibration motor 230 operates in the housing 220 to cause vibration. In the present embodiment, the vibration generator is exemplified by the vibration motor 230.

The housing 220 includes a substantially L-shaped supporting housing 223, a clamping arm 224 situated above the supporting housing 223, and a hinge 225 situated between the supporting housing 223 and the clamping arm 224. The supporting housing 223 includes a storage portion 221, in which the vibration motor 230 is stored, and a supporting plate 226, which extends from the storage portion 221. The supporting plate 226 extends in a direction away from a patient.

The clamping arm 224 is arranged along the supporting plate 226. The clamping arm 224 includes a proximal end 227, and a distal end 228 situated between the patient and the proximal end 227. The hinge 225 supports the clamping arm 224 between the proximal and distal ends 227, 228.

The dental vibration applicator 200 includes an elastic member such as a flat spring (not shown) which presses against the clamping arm 224. The distal end 228 is biased towards the supporting housing 223 by the elastic member. The proximal end 227 moves away from the supporting plate 226 due to the elastic member and the hinge 225. The distal end 228 moves away from the supporting housing 223 on the basis of the principle of a lever if a user operates the clamping arm 224 so that the proximal end 227 gets closer to the supporting plate 226.

The dental vibration applicator 200 further includes a transmission arm 222 and a bracket 310. The transmission arm 222 has an arm 290 including a proximal end 241, which is clamped by the clamping arm 224 and the supporting housing 223, and a distal end 242, which is coupled to the arm 290 and the bracket 310. The distal end 242 is situated on the opposite side of the proximal end 241.

The bracket 310 is attached to a patient's tooth. Vibration generated by the vibration motor 230 is transmitted to the patient's tooth through the transmission arm 222 and the bracket 310.

Figure 16:
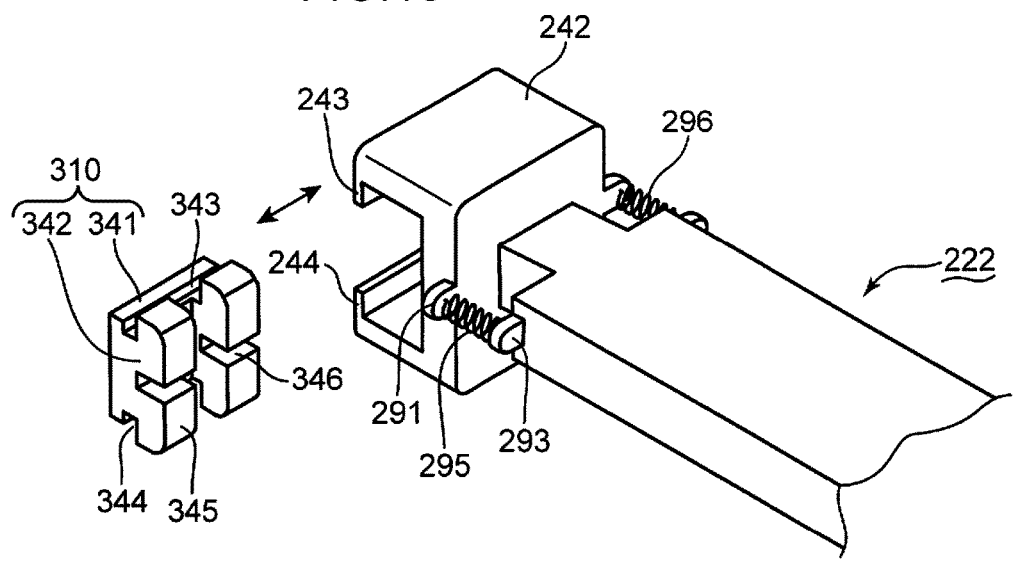
FIG. 16 is a partial enlarged view of a transmission arm of the dental vibration applicator shown in FIG. 15.

FIG. 16 is a partial enlarged view of the transmission arm 222. The transmission arm 222 is further described with reference to FIG. 16.

The bracket 310 includes a base portion 341 adhered to the outer surface of the patient's tooth and a Y-shaped piece 342 which protrudes forward from the base portion 341. An upper groove 343 and a lower groove 344 are formed between the Y-shaped piece 342 and the base portion 341. The lower groove 344 is situated below the upper groove 343.

The bracket 310 includes a front surface 345 opposite to the base portion 341. A horizontally extending front groove 346 is formed in the front surface 345. An orthodontic wire is inserted into the front groove 346. The orthodontic wire is used to apply a static load to the dentition.

The distal end 242 of the transmission arm 222 is formed substantially in C-shape. The distal end 242 includes an upper claw 243 inserted into the upper groove 343 and a lower claw 244 inserted into the lower groove 344. The distal end 242 may be slid and connected to the bracket 310. Alternatively, the distal end 242 may be engaged with the bracket 310 by a snap-fitting manner.

Figure 17:
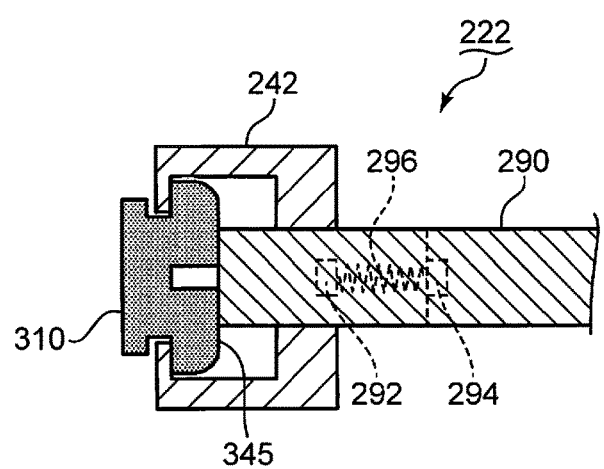
FIG. 17 is a partial cross-sectional view of the transmission arm shown in FIG. 16.

FIG. 17 is a partial cross-sectional view of the transmission arm 222. The transmission arm 222 is further described with reference to FIGS. 16 and 17.

As shown in FIG. 17, the arm 290 is inserted through the distal end 242. Therefore, the distal end 242 may be displaced along the arm 290. The distal end of the arm 290 is in contact with the front surface 345 of the bracket 310 when the distal end 242 is connected to the bracket 310.

The distal end 242 includes a left protruding piece 291, which protrudes to the left, and a right protruding piece 292, which protrudes to the right. The arm 290 includes a left protruding piece 293, which protrudes to the left, and a right protruding piece 294, which protrudes to the right. The transmission arm 222 includes a left spring 295, which is situated between the left protruding pieces 291, 293, and a right spring 296, which is situated between the right protruding pieces 292, 294. The left and right springs 295, 296 bias the distal end 242 towards the bracket 310. Therefore, the distal end 242 and the arm 290 are suitably pressed against the bracket 310. In the present embodiment, the biasing portion is exemplified by the left and right springs 295, 296.

Sixth Embodiment

The biasing force acting on the teeth may be obtained from another element except for a spring. A contacting instrument which uses threads is described in the sixth embodiment.

Figure 18:
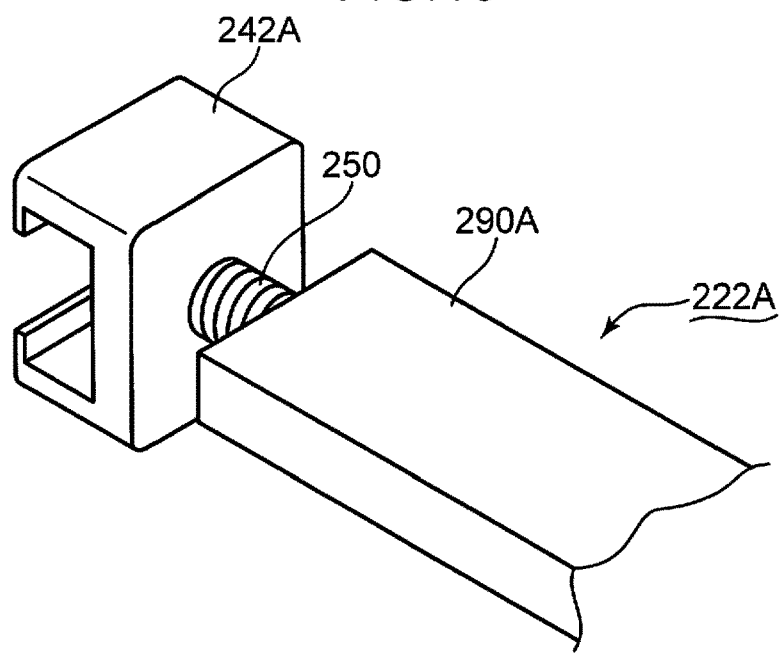
FIG. 18 is a partial enlarged view of an alternative transmission arm (the sixth embodiment).

FIG. 18 is a partial enlarged view of a transmission arm 222A. The transmission arm 222A is further described with reference to FIGS. 16 and 18.

The transmission arm 222A shown in FIG. 18 may be used instead of the transmission arm 222 described with reference to FIG. 16. Therefore, the description in the fifth embodiment is applicable to the sixth embodiment except for the transmission arm 222A.

The transmission arm 222A includes an arm 290A, a distal end 242A and a threaded portion 250. The threaded portion 250 is fixed to the distal end of the arm 290A. The distal end 242A is screwed onto the threaded portion 250.

The distal end 242A is formed substantially in C-shape like the fifth embodiment. The distal end 242 includes the upper claw 243, which is inserted into the upper groove 343, and the lower claw 244, which is inserted into the lower groove 344.

Figure 19:
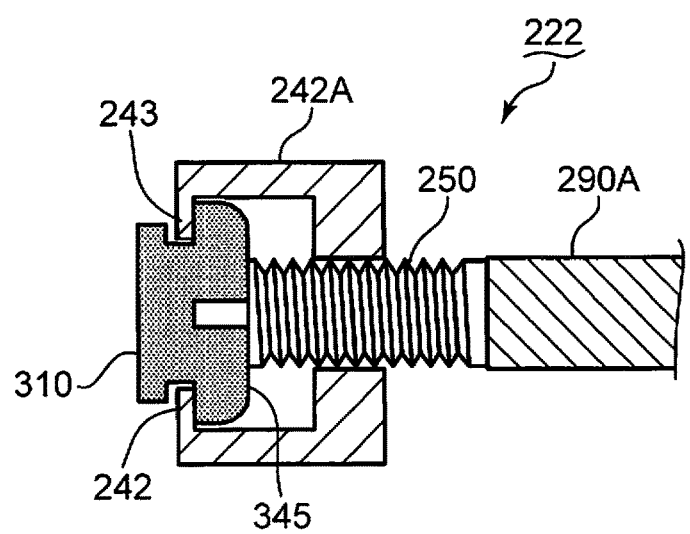
FIG. 19 is a partial cross-sectional view of the transmission arm shown in FIG. 18.

FIG. 19 is a partial cross-sectional view of the transmission arm 222A. The transmission arm 222A is further described with reference to FIGS. 18 and 19.

The distal end 242A is engaged with the bracket 310 by the upper and lower claws 243, 244, like the fifth embodiment. A user may then rotate the arm 290A to contact the threaded portion 250 with the front surface 345. Accordingly, the distal end 242A and the threaded portion 250 are pressed against a tooth, to which the bracket 310 is attached. In the present embodiment, the biasing portion is exemplified by the threaded portion 250.

The various technologies described in the context of the aforementioned embodiments mainly include the following features.

The vibration application method according to one aspect of the aforementioned embodiments includes steps of: contacting a contact portion with at least one of teeth, and vibrating the contact portion so as to give the contact portion displacement of no less than 0.04 μm.

According to this configuration, the contact portion contacted with at least one tooth is displaced by 0.04 μm or more. Therefore, the tooth of a patient under orthodontic treatment may also be displaced by 0.04 μm or more. Since the periodontal ligament is suitably stimulated, it takes a shorter time for orthodontic treatment than in prior arts.

This value (0.04 μm) comes from estimation results about displacement of human teeth under application of vibrations of 3 gf and 100 Hz, which has been effective in the aforementioned experiment using the beagle dogs, on the basis of a dynamic model of the teeth shown in Non-Patent Document 5. In this estimation, each of dynamic parameters were assumed as follows: the mass element $m_1$ representing a teeth weight=5.0 g, the mass element $m_2$ representing a weight of a portion supporting the teeth=$2.0 \times 10^3$ g, the elasticity element k representing the elasticity of periodontal ligament and root portion=$1.4 \times 10^6$ N/m, the viscosity element $c_1$ representing viscosity of the same=87.2 Ns/m, and the viscosity element $c_2$ representing the viscosity of the same=1357.1 Ns/m. These values are used for the upper first molars which has the largest volume among the teeth. This means that a displacement amount of the upper first molars per a vibrational load is the smallest. The average values shown in Non-Patent Literature 7 were referred for comparing sizes of the teeth. Each of the aforementioned dynamic parameters was calculated from each of the dynamic parameters of the upper central incisors shown in Non-Patent Literature 5 and a size ratio of the upper first molars to the upper central incisors shown in Non-Patent Literature 7.

The following assumptions were used for calculation of each of the aforementioned dynamic parameters. It was assumed that the mass element $m_1$ arising from a tooth weight was proportional to a tooth volume. It was assumed that the mass element $m_2$ arising from a weight of portions supporting the teeth was independent from a tooth size. It was assumed that the elasticity element k arising from the elasticity of the periodontal ligament and root portion and the viscosity elements $c_1$ and $c_2$ arising from the viscosity are proportional to a tooth surface area. This is based on an assumption that a thickness of the periodontal ligament is independent from the tooth. In addition, the average values of a length of the crowns of the upper first molars and upper central incisors, a width of the crowns and a total length of the teeth were based on Non-Patent Literature 7. A tooth volume was defined as "crown length×crown width×tooth total length". Tooth surface area was defined as "square of the cube root of tooth volume". The reference teeth sizes, respective dynamic parameters and displacement of the upper first molars are shown in FIG. 20. The displacement is 0.04 μm as shown in FIG. 20.

In the aforementioned configuration, a difference between a maximum value and a minimum value of a vibrational load may be no less than 3 gf and no more than 10 gf during vibration of the contact portion.

The vibrational load is a vibrational load received by each tooth of a user from a device. The range of the vibrational load is a value confirmed by the present inventors that the value was effective for shortening a treatment period in the aforementioned experiment using the beagle dogs. It is expected that a treatment period is effectively shortened for humans as well in the same vibrational load range since a treatment period was effectively shortened under the same vibrational load of 3 gf for the rats and beagle dogs, and the teeth size of the beagle dogs is substantially equal to that of humans. It is also expected from the experimental results that application of vibration of 1 gf or 50 gf is less effective for shortening a treatment period.

In the aforementioned configuration, the step of contacting the contact portion with the at least one of the teeth may include contacting the contact portion with an orthodontic appliance attached to the at least one of the teeth.

As clearly shown by the aforementioned embodiments, the phrase "contacting a contact portion with at least one tooth" refers not only to "contacting the contact portion directly with at least one of the teeth" but also refers to "contacting the contact portion indirectly through an orthodontic appliance attached to at least one of the teeth".

In the aforementioned configuration, the vibration application method may further include a step of preparing at least one device selected from a group consisting of a mouthpiece, a bite plate and a vibration probe. The at least one device may include the contact portion.

The principle of the aforementioned embodiments allows usage of various devices such as a mouthpiece, a bite plate and a vibration probe. Therefore, there is suitable orthodontic treatment.

In the aforementioned configuration, vibration of the contact portion has a wave number of no less than 3600 per day.

The wave number refers to the number of vibrations. The wave number refers to how many times the periodontal ligament is deformed if the vibration suitably propagate to the periodontal ligament.

The value of this wave number is a value confirmed by the aforementioned experiment using the rats that the value has been effective for shortening a treatment period. The present invention accelerates resorption of the alveolar bone by the osteoclasts on the compression side of the alveolar bone and addition of bone by the osteoblasts on the tension side by vibration giving deformation to the periodontal ligament.

Therefore, the wave number is independent from the size of the teeth or body. It is expected that the wave number range effective for shortening a treatment period is the same between rats and humans. Since substantially the same effects of shortening a treatment period were obtained under application of vibrations having wave numbers of 3600, 10800, 36000 and 108000, there is no upper limit on the value of the wave number of vibrational stimulation for shortening a treatment period. Accordingly, it is expected that it is less influential to the effects of shortening a treatment period whether the wave number is a large value or a small value if an appropriate number of stimulation is applied to the periodontal ligament.

In the aforementioned configuration, the step of vibrating the contact portion may be repeated at intervals of no less than one week.

The intervals are a value confirmed by the aforementioned experiment using the rats that the value has been effective for shortening a treatment period.

In the aforementioned configuration, a vibration period of the contact portion may be no less than 1 minute and no more than 30 minutes per day.

The application time range is a value confirmed by the aforementioned experiment using the rats that the value has been effective. The present invention accelerates resorption of the alveolar bone by the osteoclasts on the compression side of the alveolar bone and addition of bone by the osteoblasts on the tension side by vibration giving deformation to the periodontal ligament. Therefore, the vibration application period does not depend on a size of the teeth or body. It is expected that the wave number range effective for shortening a treatment period is substantially the same between rats and humans. It is expected that differences in application period from 1 to 30 minutes are less influential to the time-reduction effect if the aforementioned suitable range of vibration is applied since substantially the same effects of shortening a treatment period was obtained under application of vibrations for 3 minutes and 30 minutes.

The dental vibration applicator according to another aspect of the aforementioned embodiments may include a contacting instrument including a contact portion which contacts at least one of teeth or an orthodontic appliance that is attached for orthodontic treatment of the at least one of the teeth, and a vibration generator configured to vibrate the contact portion. The contact portion is displaced by no less than 0.04 μm during vibration caused by the vibration generator.

The dental vibration applicator may be used in combination with orthodontic treatment using a continuous force.

Since there is the alveolar bone around the periodontal ligament, it is difficult to apply a vibrational load directly to the human periodontal ligament. Accordingly, practically, strain is applied indirectly to the periodontal ligament by application of a vibrational load to the alveolar mucosa, erupted teeth or an orthodontic appliance attached to the dentition of a user.

Vibration is preferably applied to the teeth or an orthodontic appliance attached to the dentition of a user since transmission of vibration is weakened by gingiva and alike acting as a damper to prevent the vibrational load from being efficiently applied to the periodontal ligament if a vibrational load is applied directly to the alveolar mucosa.

A contact portion in contact with at least one of the teeth is displaced by 0.04 μm or more. Therefore, the tooth of a patient under orthodontic treatment may be displaced by 0.04 μm or more. Since the periodontal ligament is suitably stimulated, it takes a shorter time for orthodontic treatment than prior arts.

In the aforementioned configuration, the contacting instrument may be a mouthpiece which at least partially covers the at least one of the teeth.

According to the aforementioned configuration, vibration is suitably transmitted to at least one of the teeth through a mouthpiece which at least partially covers the at least one of the teeth.

In the aforementioned configuration, the contacting instrument may be a probe including a proximal end connected to the vibration generator and a distal end opposite to the proximal end. The distal end may be used as the contact portion.

According to the aforementioned configuration, vibration is suitably transmitted to at least one of the teeth through the probe.

In the aforementioned configuration, the contacting instrument may be a bite plate fixed in an oral cavity by occlusion.

According to the aforementioned configuration, vibration is suitably transmitted to at least one of the teeth through the bite plate.

In the aforementioned configuration, the dental vibration applicator may further include a biasing portion which biases the contact portion towards the at least one of the teeth.

According to the aforementioned configuration, since the contact portion is biased towards at least one of the teeth by the biasing portion, vibration is suitably transmitted to at least one of the teeth.

INDUSTRIAL APPLICABILITY

The principle of the aforementioned various embodiments may be applicable to technologies relating to orthodontic treatment.

The invention claimed is:

1. A vibration application method comprising steps of:
    contacting a contact portion with at least one of teeth or an orthodontic appliance that is attached for orthodontic treatment of the at least one of the teeth; and
    vibrating the contact portion so that the contact portion displaces by no less than 0.04 μm under a condition in which the contact portion is fixed onto the at least one of the teeth or the orthodontic appliance,
    wherein vibration of the contact portion has a wave number of no less than 3600 per day,
    wherein a difference between a maximum value and a minimum value of a vibrational load which is given the at least one of teeth or the orthodontic appliance is no less than 3 gf and no more than 6 gf during the vibration of the contact portion, and
    wherein a combination of the wave number and the difference activates metabolism of periodontal ligament and alveolar bone to shorten a period of orthodontic treatment.

2. The vibration application method according to claim 1, further comprising a step of preparing at least one device selected from a group consisting of a mouthpiece, a bite plate and a vibration probe,
    wherein the at least one device includes the contact portion.

3. The vibration application method according to claim 2, wherein the step of vibrating the contact portion is repeated at intervals of no less than one week.

4. The vibration application method according to claim 2, wherein a vibration period of the contact portion is no less than 1 minute and no more than 30 minutes per day.

* * * * *